(12) United States Patent
Win et al.

(10) Patent No.: US 8,909,339 B2
(45) Date of Patent: Dec. 9, 2014

(54) GLUCOSE POWERED IMPLANTABLE DEVICE TO COLLECT BLOOD INGREDIENTS

(75) Inventors: Jux Win, Jebei (TW); Wei-Leun Fang, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 6 days.

(21) Appl. No.: 13/609,902

(22) Filed: Sep. 11, 2012

(65) Prior Publication Data

US 2014/0052210 A1 Feb. 20, 2014

(30) Foreign Application Priority Data

Aug. 15, 2012 (TW) .............................. 101129587 A

(51) Int. Cl.
  *A61N 1/378* (2006.01)
(52) U.S. Cl.
  USPC ............................................ 607/35; 600/505
(58) Field of Classification Search
  CPC ..... A61B 5/0215; A61B 5/6876; H01M 8/16; H01M 8/22
  USPC .................... 607/5, 35, 2; 600/485, 505, 549; 429/213
  See application file for complete search history.

(56) References Cited

U.S. PATENT DOCUMENTS

| | | | |
|---|---|---|---|
| 3,941,135 A * | 3/1976 | von Sturm et al. | 607/35 |
| 6,131,581 A * | 10/2000 | Leysieffer et al. | 128/899 |
| 6,470,212 B1 * | 10/2002 | Weijand et al. | 607/35 |
| 7,167,756 B1 * | 1/2007 | Torgerson et al. | 607/61 |
| 2003/0168861 A1 * | 9/2003 | Estevez | 290/1 R |
| 2004/0043052 A1 * | 3/2004 | Hunter et al. | 424/426 |
| 2004/0245101 A1 * | 12/2004 | Willner et al. | 204/403.01 |
| 2010/0206750 A1 * | 8/2010 | Tonks | 205/777.5 |
| 2010/0298720 A1 * | 11/2010 | Potkay | 600/485 |

* cited by examiner

*Primary Examiner* — Eric D. Bertram
*Assistant Examiner* — Pamela M Bays
(74) *Attorney, Agent, or Firm* — Birch, Stewart, Kolasch & Birch, LLP

(57) ABSTRACT

An implantable device that includes a plurality of conduits, a plurality of chambers, and a control unit. The blood through the plurality of conduits and the chambers collect the ingredient information of the blood according to the blood through the conduits. The chambers transfer the ingredient information of the blood to the control unit to analysis. The chamber includes two electrodes, the chamber exploits a reverse theorem to force the glucose of the blood generates a plurality of charges flowing between the electrodes and further to generate a current in the chamber. Thus, the implantable device can achieve the goal of the self-electricity-generation.

7 Claims, 4 Drawing Sheets

GLUCOSE POWERED IMPLANTABLE DEVICE TO COLLECT BLOOD INGREDIENTS

TECHNICAL FIELD

The present invention relates to a biomedical device, more especially a perpetual implantable biomedical micro-device.

BACKGROUND

The conventional pacemaker is bulky and requires an invasive surgery to implant into the patient's chest or abdominal position. Currently, the lifetime of the lithium battery of the pacemaker is around 5 years. In other words, patients have to require a hospitalization for every five years to replace the new battery of the pacemaker in order to ensure the normal work of the pacemaker work normally. Therefore, patients must repeatedly tolerate the discomfort of the surgery and bear the high risk of the invasive surgery.

The conventional implantable pacemaker is packaged implanted into the body with the control circuit. In order to function correctly, the control circuit is connected to the organ which need to be triggered (such as, from head vein to the heart muscle) via plurality of wires. And, in order to elaborate the function of the pacemaker and to provide an appropriate current to execute the defibrillation function when the frequency in occurrence of ventricular pulse or fibrillation are occurred, even some pacemakers require 3 or more wires to connect the control unit with the organ.

Features of the wire number and the wire length of the control unit in conjunction with the pacemaker could easily cause a larger burden on the patient's body. Moreover, due to the distance between the conventional pacemaker and the organ is too far and the conventional pacemaker only has single function, so that the conventional pacemaker can not record the life information (such as blood amount and oxygen content, etc) of the organ and send the related information to the internal system or external medical instrument immediately and thus can not take the proper action in real time. When the dysfunction of the organ (such as, heart) is occurred or the original function varied over a certain range and make the organ function damaged, the patient need an emergency with the outside support (such as, electric shock) but sometimes the outside support causing patients more harm.

SUMMARY

One of the purposes of the invention is to disclose an implantable device configured in a blood vessel, comprises a plurality of conduits allow a part of blood flowing through, a plurality of chambers configured between said plurality of conduits and operable for collecting one or more information of said blood, wherein, said plurality of chambers each comprises two electrodes to generate a current according to said blood and so as to generate an electric power, and a control unit operable for analyzing said one or more information collected by said plurality of chambers.

BRIEF DESCRIPTION OF THE DRAWINGS

Features and advantages of embodiments of the subject matter will become apparent as the following detailed description proceeds, and upon reference to the drawings, wherein like numerals depict like parts, and in which.

DETAILED DESCRIPTION

Reference will now be made in detail to the embodiments of the present invention. While the invention will be described in conjunction with these embodiments, it will be understood that they are not intended to limit the invention to these embodiments. On the contrary, the invention is intended to cover alternatives, modifications and equivalents, which may be included within the spirit and scope of the invention.

Furthermore, in the following detailed description of the present invention, numerous specific details are set forth in order to provide a thorough understanding of the present invention. However, it will be recognized by one of ordinary skill in the art that the present invention may be practiced without these specific details. In other instances, well known methods, procedures, components, and circuits have not been described in detail as not to unnecessarily obscure aspects of the present invention.

Figure 1:
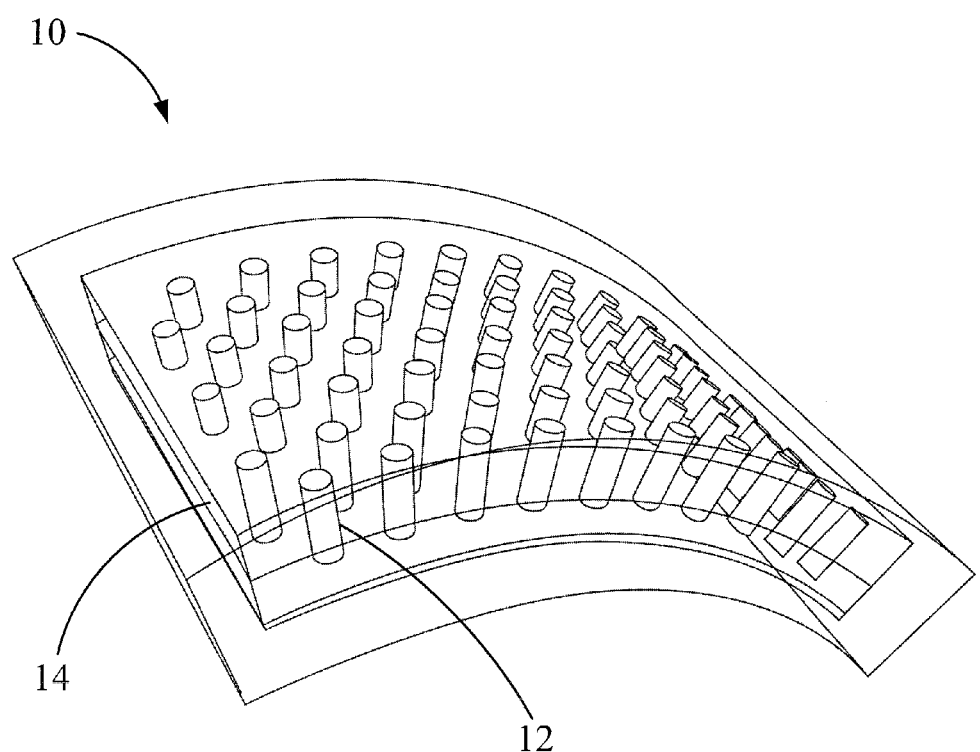
FIG. 1 illustrates an implantable device in accordance with one embodiment of the present invention.

FIG. 1 illustrates an implantable device 10 in accordance with one embodiment of the present invention. The implantable device 10 includes a plurality of conduits 12, a plurality of chambers 14 (formed by flexible substrates, but not limited to), and a control unit (not shown). The plurality of conduits 12 allow at least parts of blood flowing through. The plurality of chambers 14 collect the ingredient of the blood according to the blood which flowing through the conduits 12. The chambers 14 transfer the ingredient information of the blood to the control unit for further analysis.

Figure 2:
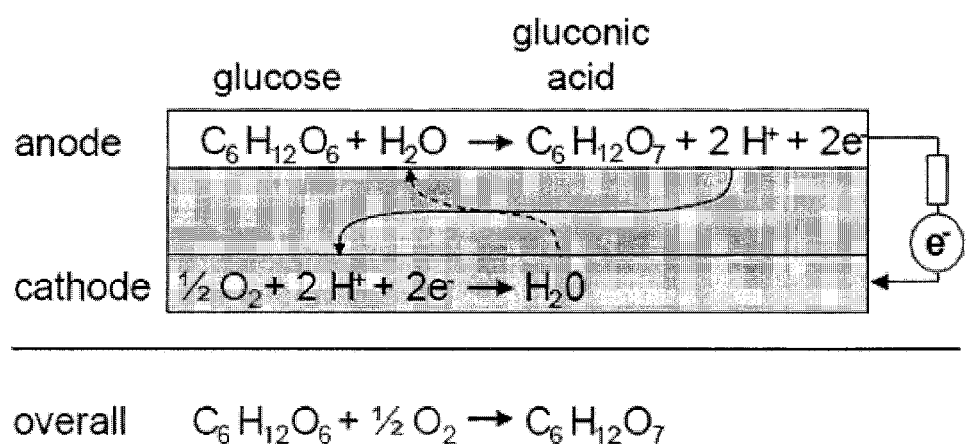
FIG. 2 illustrates a reverse theorem which a chamber in accordance with one embodiment of the present invention exploits to generate an electric power by blood.

The plurality of chambers 14 each comprises two electrodes (formed by porous structure, but not limited to). Please refer to FIG. 2 which illustrates a reverse theorem which a chamber in accordance with one embodiment of the present invention exploits to generate an electric power by blood. The plurality of chambers 14 exploit a reverse theorem to force the glucose ingredient of the blood generates a plurality of charges flowing between two electrodes of each chamber 14. A current is generated according to the flowing charges so as to generate an electric power. The generated electric power can be applied to the implantable device 10 to achieve the goal of the self-electricity-generation. The plurality of chambers 14 further includes a capacitor (not shown) with macromolecules material for storing the generated electric power.

Figure 3:
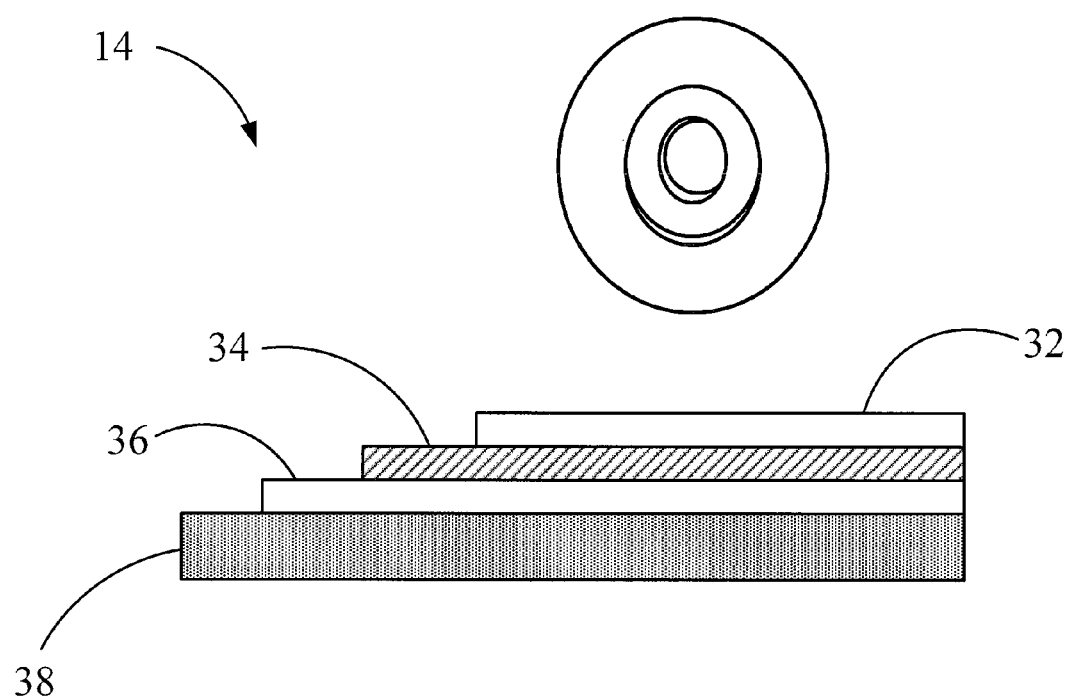
FIG. 3 illustrates a chamber in accordance with one embodiment of the present invention.

FIG. 3 illustrates a chamber in accordance with one embodiment of the present invention. The plurality of chambers 14 each includes a substrate 38 (such as flexible substrate, but not limited to). In one embodiment, the substrate 38 has the advantage of bio-compatibility and the function of the dialysis. Thus, Poly-Methyl-Methacrylate (PMMA) is a suitable material of the substrate 38. An electrode 36 is plated on the substrate 38 by a thermal coating method, and a film 34 is covered above the electrode 36 to define an area of the electrode 36. And then, an electrode 32 is thermal-coated on the film 34 so as to form a unique chamber 14. Due to the substrate 38 is flexible, the chamber 14 can be bended and even can be rolled up as a pillar. Therefore, the plurality of chambers 14 shown in FIG. 3 can be rolled up as a pillar structure which the electrode 32 is exposed to the outside surface of the pillar. The outside electrode 32 can increase the area which contacts with the blood flowing through the plurality of conduits 12 of the implantable device 10, so as to improve the efficiency of energy storing and the power generating by increase the amount of the flowing glucose.

In one embodiment, the control unit can be a micro processor and includes an analog circuit (not shown) and a digital circuit (not shown), the control unit can provide power supply and conversion function, the control unit can provide voltage regulation of charge/discharge, voltage up-covert, information analysis of the heart beat or blood related, the function of the power storage and transformation and self-detect function by cooperate with the chamber 14, but not limited to.

In one embodiment, the implantable device 10 can be implanted into the blood vessel which besides the monitor-desired organ. The implantable device 10 can monitor and transfer the ingredient of the blood, generate the electric power by itself and store the power. Therefore, the implantable device 10 can be implanted perpetual and without battery change.

Figure 4:
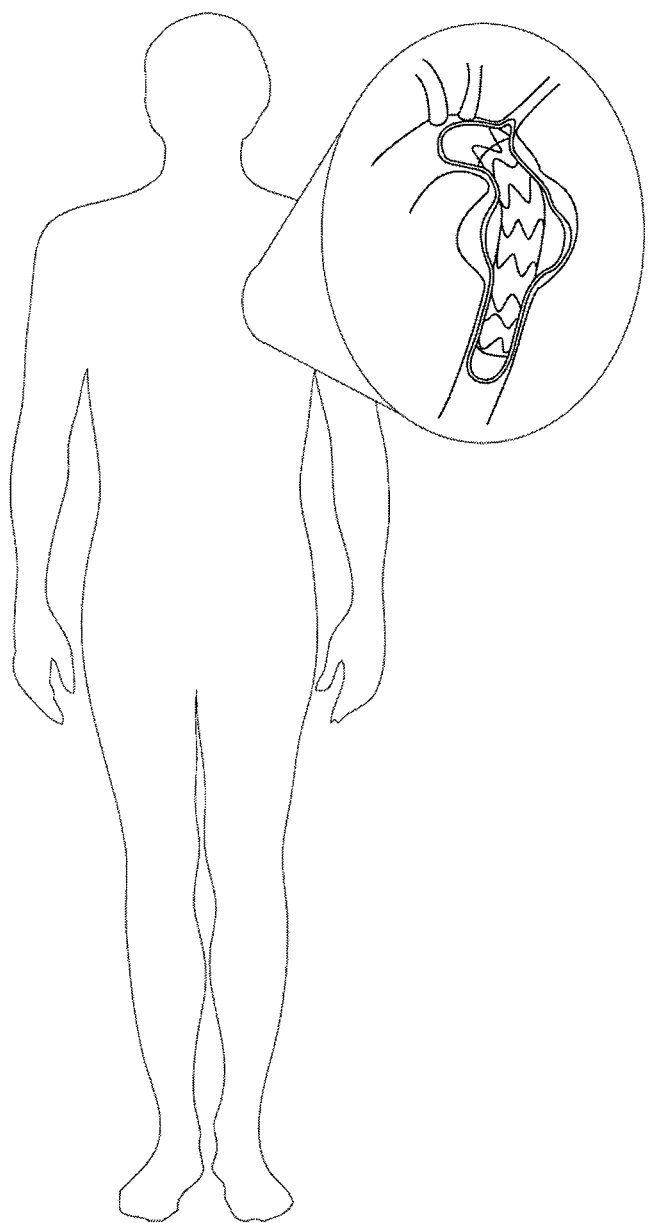
FIG. 4 illustrates an implantable device implanted into blood vessel in accordance with one embodiment of the present invention.

FIG. 4 illustrates an implantable device implanted into blood vessel in accordance with one embodiment of the present invention. For illustration, the embodiment is illustrating an implantable device implanted into a blood vessel which near the heart. The present invention is not limited to implanted near the heart, any organ needs to be monitored can be applied. In one embodiment, the implantable device 10 is implanted into the blood vessel which beside the heart, the implantable device 10 not only monitoring the function of the heart and regulating the rhythm of the heart, but also executing the function setup via the external control, such as, mode setting by external wireless control, or manipulating the control unit to access the information of the heart and analysis the function of the heart by remote control from external.

In one embodiment, the control unit includes a wireless module (not shown), the wireless module can transfer the blood information to an external system (not shown) and also receives an external setting command. The external system can setup an urgent mode for the implantable device 10. When the information of the heart illustrates abnormal condition (such as, the blood amount or the oxygen content are decreasing, but not limited to) for a time period (such as, 3 minutes, but not limited to, can be setting by medical center or according to the advice of the doctor), the implantable device 10 can enable the corresponding action (such as, an electric shock), the implantable device 10 can increase a voltage and outputs that voltage to heart immediately for low-level first aid. Advantageously, the patient can be rescue before he/she falls unconscious due to lack of oxygen.

In this embodiment, the plurality of chambers 14 of the implantable device 10 each further includes an inductor (such as, a sensing winding, not shown in the figures). The inductor can sense the external charge power via the wireless module of the control unit.

In one embodiment, the outer of the implantable device 10 is molded by a macromolecules material, such as dialysis film and Dacron for molding and suturing with the blood vessel propose, but not limited to.

Accordingly, the present invention is to provide an implantable device which uses the blood of the human himself to generate minor electric power and to regulate the rhythm of the heart. The electric power is generated base on the requirement of the adequate voltage to force the heart beat. Therefore, the size of the implantable device can be minimized and can be fixed in the blood vessels which near the required organ (such as, heart, bladder, liver, kidney, but not limited to). The implantable device can work permanent without change the battery due to its self-electricity-generation function.

While the foregoing description and drawings represent embodiments of the present invention, it will be understood that various additions, modifications and substitutions may be made therein without departing from the spirit and scope of the principles of the present invention. One skilled in the art will appreciate that the invention may be used with many modifications of form, structure, arrangement, proportions, materials, elements, and components and otherwise, used in the practice of the invention, which are particularly adapted to specific environments and operative requirements without departing from the principles of the present invention. The presently disclosed embodiments are therefore to be considered in all respects as illustrative and not restrictive, and not limited to the foregoing description.

What is claimed is:

1. An implantable device to be placed within a blood vessel, comprising:
   a plurality of conduits configured to allow a part of blood in the blood vessel to flow through the conduits;
   a plurality of chambers located between said plurality of conduits and configured to collect one or more ingredient of said blood, wherein each of said plurality of chambers is a pillar structure and comprises:
   a flexible substrate;
   a first electrode directly disposed on and in contact with the flexible substrate;
   a film directly disposed on and in contact with the first electrode; and
   a second electrode directly disposed on and in contact with the film, the film being sandwiched between the first electrode and the second electrode,
   wherein a combination of the flexible substrate, the first electrode, the film and the second electrode is rolled up as the pillar structure, the second electrode is an outermost layer of the pillar structure surrounding the flexible substrate, the first electrode and the film, and is a porous structure thereby increasing an amount of glucose flowing therethrough, and each of said plurality of chambers is configured to use glucose in said blood to generate a current flowing between the first electrode and the second electrode so as to generate an electric power; and
   a control unit analyzing said one or more ingredient of said blood collected by said plurality of chambers.

2. The implantable device as claimed in claim 1, wherein each of said plurality of chambers further comprises a capacitor to store said electric power generated by said current.

3. The implantable device as claimed in claim 1, further comprising: an antenna module transmitting said one or more ingredient of said blood to an external system.

4. The implantable device as claimed in claim 3, wherein said antenna module receives an external setting command from said external system.

5. The implantable device as claimed in claim 1, further comprising:
   a dialysis film covering said implantable device.

6. The implantable device as claimed in claim 5, wherein said dialysis film is a polymer material.

7. The implantable device as claimed in claim 1, wherein said control unit is a micro processor.

* * * * *